(12) United States Patent
Hochrainer et al.

(10) Patent No.: US 7,314,187 B2
(45) Date of Patent: Jan. 1, 2008

(54) ATOMIZER FOR APPLYING LIQUIDS ONTO EYES

(75) Inventors: Dieter Hochrainer, Schmallenberg (DE); Bernd Zierenberg, Bingen (DE); Michael Diestelhorst, Cologne (DE); Isolde Martin, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/457,506

(22) Filed: Jul. 14, 2006

(65) Prior Publication Data

US 2006/0258993 A1    Nov. 16, 2006

Related U.S. Application Data

(63) Continuation of application No. 10/601,737, filed on Jun. 23, 2003, which is a continuation of application No. 10/185,949, filed on Jun. 28, 2002, now abandoned.

(60) Provisional application No. 60/348,785, filed on Oct. 23, 2001.

(30) Foreign Application Priority Data

Jun. 29, 2001 (DE) .................... 101 31 178

(51) Int. Cl.
*B05B 9/043* (2006.01)

(52) U.S. Cl. .......... 239/333; 239/349; 239/533.15; 239/571; 239/583; 222/383.1; 222/385; 222/401; 137/533; 137/533.23; 128/200.14; 604/289; 604/521

(58) Field of Classification Search ........... 239/333, 239/320, 321, 329, 337, 338, 288, 288.3, 239/288.5, 349, 533.1, 533.15, 571, 583, 239/570; 222/162, 340, 341, 383.1, 373, 222/379, 385, 401, 402; 604/521, 289; 137/533.17; 128/200.14
See application file for complete search history.

(56) References Cited

U.S. PATENT DOCUMENTS

| 5,037,406 A | * | 8/1991 | Smith et al. ............. 604/301 |
| 5,201,726 A | * | 4/1993 | Kirkham ................. 604/294 |
| 5,497,944 A | * | 3/1996 | Weston et al. ........... 239/321 |
| 5,578,021 A | * | 11/1996 | Cornish ................. 604/300 |
| 5,964,416 A | * | 10/1999 | Jaeger et al. ............ 239/333 |

OTHER PUBLICATIONS

Hochrainer et al., Comparison of the Aerosol Velocity and Spray Duration of Respimat® Soft MistTM Inhaler and Pressurized Metered Dose Inhalers, J. Aerosol Med., vol. 18, No. 3 (2005).

* cited by examiner

*Primary Examiner*—Dinh Q. Nguyen
(74) *Attorney, Agent, or Firm*—Michael P. Morris; Mary-Ellen M. Devlin; Thomas C. Blankinship

(57) ABSTRACT

Atomizers for administering liquids to the cornea or conjunctiva of the eye, special eye adapters for atomizers and the use of atomizers for ophthalmological administration. The atomizers are free from propellant gas and have an energy reservoir for supplying the energy needed for the atomization process.

4 Claims, 3 Drawing Sheets

ATOMIZER FOR APPLYING LIQUIDS ONTO EYES

This Application is a continuation of U.S. patent application Ser. No. 10/601,737, filed on Jun. 23, 2003, which is a continuation of U.S. patent application Ser. No. 10/185,949, filed on Jun. 28, 2002 now abandoned, which is an application claiming the benefit under 35 USC 119(e) of U.S. Prov. App. No. 60/348,785, filed on Oct. 23, 2001. This Application also claims priority of foreign application DE 10131178, filed on Jun. 29, 2001. This Application incorporates these priority applications by reference in their entireties.

The present invention relates to atomisers for applying liquids to the cornea of the eye or to the connective tissue of the eye, special eye adapters for atomizers and the use of atomizers for ophthalmological administration. The atomizers according to the invention are free from propellant gas and have an energy reservoir for supplying the energy required for the atomizing process.

PRIOR ART

For treating dry eyes, for moistening the surface of the eye for contact lens wearers, for numerous eye diseases or methods of investigating the eye it is usual to administer medicaments in the form of an aqueous formulation as eye drops. For this form of administration, liquid dispensers have been developed in which the formulation is supplied from a storage bottle through a dropper, for example (dropper bottles or EDO-Ophthiols). The aqueous formulation usually flows out of the dropper opening as a result of manual pressure being applied to the compressible storage bottle. First, a drop forms on the opening, which does not break away from the dropper and drop into the eye until a certain relationship is reached between the size of the dropper opening, the surface tension and the weight of the drop. Usually, aqueous eye drops have a volume of about 0.05 ml.

This method of dropping liquids onto the eye has various disadvantages. On the one hand, not all patients find it easy to administer drops of liquid into their own eyes. This is partly because they have to lean their head back (recline the head) and then let the drop fall into the eye from above. Children and old people in particular find this very difficult.

In addition, it happens occasionally that a patient will accidentally stick the applicator of the dropper bottle into their eye.

A further disadvantage is that the formulation administered is initially only applied to one point on the cornea, which feels unpleasant, not only because of the local pressure produced on the surface of the eye.

Often, the patients themselves cannot tell whether they have successfully administered the prescribed amount of eye drops or not. As a rule a patient only realizes whether any liquid has reached the target organ when an excess of the formulation comes out of the eye and is noticed, for example, either by tasting it or as liquid on the cheeks. However, once this stage has been reached, an excessive dose has already been given, which may lead to unwanted systemic side effects.

In connection with this, it is important to note that the surface of the eye is coated with about 7 microlitres of a film of liquid. Any application of an additional liquid consequently causes some of the total liquid on the eye to flow away through the tear duct. This naturally occurs particularly when larger amounts of liquid, such as e.g. 40 microlitres or more of eye drops are applied. If a pharmacologically effective liquid enters the tear duct, it can be absorbed systemically by the body, i.e. the pharmacologically active ingredients are absorbed directly by the body. This may lead to allergic or toxicological effects. In conventional applications about 80% of the liquid administered is displaced out of the eye and some of it enters the tear duct.

Another disadvantage is that during the instilling of the drops the patient has to consciously fight their blink reflex. If they do not manage to do so, the formulation is delivered not to the eye but to the eyelid and further drops have to be given, which may in turn lead to overdosing with the consequences described above and cause undesirable systemic side effects.

Another disadvantage of this method is that there may be short-term irritation of the eyes at the site where the drops are instilled.

The conventional application devices are also not protected against the entry of germs into the formulation for administration, which means that preservatives have to be added to the formulations. Preservatives may lead to chronic inflammation of the conjunctiva or the underlying Tenon's membrane in long-term or chronic use. There may be morphological changes in this tissue, which are a major drawback particularly in operations, as the wound healing process is disrupted and/or scarring may occur.

U.S. Pat. No. 5,588,564 discloses a pump spray provided with an adapter for administering a spray jet to the eye. As the spray duration of this system is short, there is a danger that the solution will not be sprayed onto the eye but onto the eyelid, as a result of the blink reflex. Neither the pump spray nor the adapter has means for protecting the eye from possible injury by the comparatively hard spray jet.

U.S. Pat. No. 5,921,444 discloses a spray device with a fitting for administering a liquid to an eye. The disadvantages of this system are similar to those described above.

WO 96/00050 discloses an applicator for applying liquids to an eye, wherein the spray device is located within a housing one side of which is constructed so that it can fit around an eye. The aerosol droplets produced with the device have a diameter of at least 20 micrometres. The spray duration of this system is less than $\frac{1}{20}^{th}$ of a second (page 13), which has the disadvantages described above.

EP 0911056 discloses an atomizer for placing over an eye with an adapter which has a shutter or deflector plate positioned so that the spray jet does not strike the cornea directly. However, on the one hand a protector of this kind will become dirty very quickly and is difficult to clean and on the other hand it militates against exact and reproducible metering.

DESCRIPTION OF THE INVENTION

Thus, the problem on which the present invention is based is to apply aqueous solutions or ophthalmologically effective formulations by means of a single form of application to the surface of the eye in such a way as to reduce the local irritation of one area of the cornea compared with conventional methods of applying eye drops.

Another problem is to develop a process with which eye drops can be administered in a manner which is more pleasant for the user than is known from the prior art.

Another problem is to develop a process in which the liquid to be administered can be applied uniformly over the eye.

Another problem of the invention is to minimise overdosing.

Yet another objective is to minimise the risk of injury to the eye during application of the eye drops.

The present invention solves this problem by providing atomizers which convert a small amount of the comparatively highly concentrated formulation to be applied through a nozzle into a soft spray mist with small particle sizes and travelling at low speed and bring this spray mist into contact with the surface of the eye.

The atomizers according to the invention comprise, close to the nozzle from which the spray mist emerges, an adapter which fixes the distance from the nozzle to the eye and prevents the aerosol cloud from being blown away by wind.

Another criterion for these atomizers is that the pulse of particles of spray mist leaving the adapter must not be so great that the cornea can be damaged. In other words, the force with which the aerosol mist hits the eye is not great enough to feel unpleasant and make the patient close their eyelid.

In connection with the word "force" it should be noted that, because of the large number of droplets arriving one after another in an extremely short interval, it is not the force of the individual droplets that matters but rather the force with which the cloud of droplets as a whole strikes the eye.

DETAILED DESCRIPTION OF THE INVENTION

To guarantee this, the particles leaving the nozzle of the atomizer must not exceed a certain mass and velocity, or the atomizer and adapter must be constructed so that the speed of the droplets leaving the nozzle is reduced accordingly, as they travel from the nozzle to the eye. A spray duration of at least 0.5 seconds, preferably at least 1 second, is also important, as this spreads the force of the droplets hitting the eye over a longer period, thus reducing it, and any blinking that may occur during this period will keep only a comparatively small proportion of the cloud of droplets away from the eye.

The upper limit of the force of the cloud of droplets hitting the eye should not exceed 5 milliNewtons, preferably 2.5 milliNewtons. Preferably, the force is on average less than 0.5 milliNewtons and more preferably less than 0.05 milliNewtons. Most preferably, the process according to the invention produces a spray mist which corresponds to an aerosol of water droplets with an average diameter of about 2 to 20 microns.

The forces specified correspond to a pulse of the particles with an upper limit of less than $5*10^{-4}$ kilogram*metre per second (within the scope of the present specification the symbol ^ denotes the mathematical term written as a superscript, i.e. for example $10^{-2}$ represents 0.01, etc.). Preferably, the pulse is on average between $10^{-4}$ kilogram*metre per second and $10^{-10}$ kilogram*metre per second, more preferably not more than $5*10^{-5}$ kilogram*metre per second, specifically $5*10^{-7}$ kilogram*metre per second.

In the most preferred case, a soft spray mist is produced by the process according to the invention which corresponds to an aerosol of water droplets with a mean diameter of about 1-15 microns. The preferred particle size of the aerosol is 1 to 10 microns, more preferably 3 to 8 microns. All the data relating to the particle size relates to the average particle size in the form of the average aerodynamic diameter.

By the aerodynamic diameter is meant the kinetic diameter of a gas particle or, as in this case, an aerosol droplet, which corresponds to the diameter of a sphere with a density of 1 g cm$^{-3}$, which, under the effect of external mechanical forces in equilibrium, has the same speed of migration relative to the dispersing agent (gas or air in this case) as the particles under investigation.

Within the scope of the present invention, the aerosol cloud meets the surface of the eye at a distance from the nozzle of 1 to 5 cm, preferably 1 to 3 cm, most preferably 1.5 to 2.5 cm.

The applicator according to the invention is an atomizer comprising an adapter around its nozzle for placing over the eye.

The adapter is a cavity surrounded by a wall with two openings. One opening surrounds the nozzle of the atomizer so that a spray jet leaving the nozzle is conveyed exclusively into the cavity. Preferably, the nozzle is centrally arranged within the opening. Through the second opening, which is generally opposite the first opening, the spray jet leaves the cavity to make contact with the eye. The outer contour of the second opening is preferably constructed so that it surrounds the visible part of the human eye, preferably without pressing on the surface of the eye.

To meet this criterion, this second opening is preferably of the following configuration, if the adapter is connected to the atomizer:

In plan view the openings of the adapter are round to oval in shape.

The opening closest to the eye is shaped so as to surround the eye entirely, i.e. one part of the opening is longer than the other. In cross section, the opening thus takes the form of a concave line one end of which is at a greater spacing from the nozzle than the other end.

In its simplest embodiment, the adapter is a funnel-shaped tube with two opposite openings, the opening on the tapering side surrounding the nozzle of the atomizer and thus being surrounded by the nozzle opening of the adapter. The opening on the other side of the adapter is large enough to fit around the outer contour of an eye.

The adapter may be permanently connected to the atomizer via the first opening, e.g. if the edge of this opening is welded onto part of the inhaler or if the casing of the atomizer and the adapter constitute a single component. The adapter is then an integral part of the atomizer and this first opening is then in practice only a non-open part of the atomizer.

The adapter may also be constructed as a detachable element. In this case, the atomizer may have, close to the nozzle, one or more projections onto which the adapter can be fitted over the first opening. Such a projection may be, for example, a ring surrounding the nozzle with a height ranging from a few mm to a few cm (up to 5 cm), preferably with a height from 1-2.5 cm.

The side of the adapter attached to the atomizer may be constructed so that it can be fitted directly onto the nozzle holder or is fixed to another element in the vicinity of the nozzle.

The other end of the adapter is constructed so that it can be placed on a person's face in such a way as to completely surround the visible part of the eye while covering as little of the skin of the face as possible. This ensures that the majority of the spray mist reaches the surface of the eye without wetting the facial skin very much. Preferably, the opening on this side of the adapter is oval.

On the outlet side of the adapter, openings may optionally be formed in the side wall of the adapter through which excess spray mist can escape. These openings preferably have a diameter of up to 1 cm, more preferably up to 0.5 cm.

Moreover, the adapter is designed so that it cannot damage the face or the eye.

Within the scope of the present invention, preferred atomizers are those wherein a quantity of less than 100 microlitres, preferably less than 50 microlitres, most preferably less than 20 microlitres of active substance solution can be atomized by preferably one actuation to form an aerosol with an average particle size of less than 20 microns, preferably less than 10 microns.

Preferably, atomizers as designated by the trade mark RESPIMAT® are used.

The method according to the invention is characterised inter alia in that the quantity of formulation to be administered can be restricted to a few microlitres.

An apparatus of this kind for propellant-free atomizing of a metered amount of a liquid pharmaceutical composition is described in detail, for example, in International Patent Application WO 91/14468 "Atomizing Device and Methods" and also in WO 97/12687, cf. FIGS. 6a and 6b and the associated description. In an atomizer of this kind, a pharmaceutical solution is converted into an aerosol with an average particle size (average aerodynamic diameter) of less than 20 microns, and sprayed, by the application of high pressures of up to 500 bar. Reference is specifically made to the abovementioned publications in their entirety for the purposes of the present specification.

In atomizers of this kind, the solution formulations are stored in a reservoir. It is essential that the formulations of active substance used are sufficiently stable when stored and at the same time are of a nature such that they can be administered directly for the medical purpose in question, if possible without any further manipulation. Moreover, they should not contain any ingredients which could interact with the atomizer in such a way that the atomizer or the pharmaceutical quality of the solution, or of the aerosol produced, might be harmed.

To atomize the solution, a special nozzle is used as described for example in WO 94/07607 or WO 99/16530, both of which are specifically referred to at this point.

The preferred atomizer essentially consists of an upper housing part, a pump housing, a nozzle, an adapter, a locking mechanism, a spring housing, a spring and a storage container, the outstanding features of the atomizer being:
- a pump housing which is secured in the upper housing part and which comprises at one end a nozzle body with the nozzle or nozzle arrangement,
- a hollow plunger with valve body,
- a power takeoff flange in which the hollow plunger is secured and which is located in the upper housing part,
- a locking mechanism situated in the upper housing part,
- a spring housing with the spring contained therein, which is rotatably mounted on the upper housing part by means of a rotary bearing,
- a lower housing part which is fitted onto the spring housing in the axial direction, and
- an adapter in the form of a cavity with two opposite openings, the smaller opening closely surrounding at least the point of emergence of the aerosol from the nozzle and the larger opening having a contour which enables this opening to be fitted over an eye.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 MPa (about 50 to 600 bar), preferably 10 to 60 MPa (about 100 to 600 bar) on the fluid, comprising the measured amount of active substance solution, at its high pressure end at the moment when the spring is actuated. Volumes of 10 to 50 microlitres are preferred, while volumes of 5 to 20 microlitres are particularly preferred and a volume of 15 microlitres per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed for example in WO-94/07607; reference is hereby made to the contents of this specification, particularly FIG. 1 therein and the associated description.

The nozzle body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the width is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°.

The nozzle openings are preferably arranged at a spacing of 10 to 200 microns, more preferably at a spacing of 10 to 100 microns, most preferably 20 to 50 microns. Spacings of 22 to 28 microns are most preferred. The jets will therefore meet directly in front of the nozzle openings.

As already mentioned, the liquid pharmaceutical preparation is under an entry pressure of up to 600 bar, preferably 200 to 300 bar, at the entry to the nozzle body and is atomized into an inhalable aerosol through the nozzle openings. The preferred particle sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited through two stops. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a movable, mouldable ring of plastic or metal. The ring is arranged in a plane at right angles to the atomizer axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomizer; this causes the ring to move in the annular plane. Details of the construction of the locking mechanism are given in WO 97/20590.

The lower housing part is pushed axially over the spring housing and covers the mounting, the drive of the spindle and the storage container for the fluid.

When the atomizer is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomized may be pushed into the atomizer one after another and used in succession. The storage container contains the aqueous aerosol preparation according to the invention.

The atomizing process is initiated by pressing gently on the actuating button. As a result, the locking mechanism opens up the path for the power takeoff member. The biased spring pushes the plunger into the cylinder of the pump housing. The fluid leaves the nozzle of the atomizer in atomized form.

Some of the elements of the atomizer which come into contact with the liquid being administered as it travels from the storage container to the nozzle may optionally be made of oligodynamically active ingredients or may be coated with germicidal materials. Alternatively or in addition, a germ-repellent filter may be formed in this pathway. The advantage of such embodiments is that no germs can get into the storage container from outside and therefore there is no need to add preservatives. This is particularly advantageous for long-term application, as already explained.

Further details of construction are disclosed in PCT Applications WO 97/12683 and WO 97/20590, to which reference is hereby made.

The components of the atomizer (nebulizer) are made of a material which is suitable for its purpose. The housing of the atomizer and, if its operation permits, other parts as well are preferably made of plastics, e.g. by injection moulding. For medicinal purposes, physiologically safe materials are used.

The other end of the adapter (3) is constructed so that it can be fitted over the eye socket like a negative.

As already indicated, the adapter may be of a kind in which the pulse of the particles of spray mist is reduced, particularly wherein the speed of the particles is reduced.

In the simplest case this is achieved by increasing the distance between the two openings of the adapter.

Figure 1:
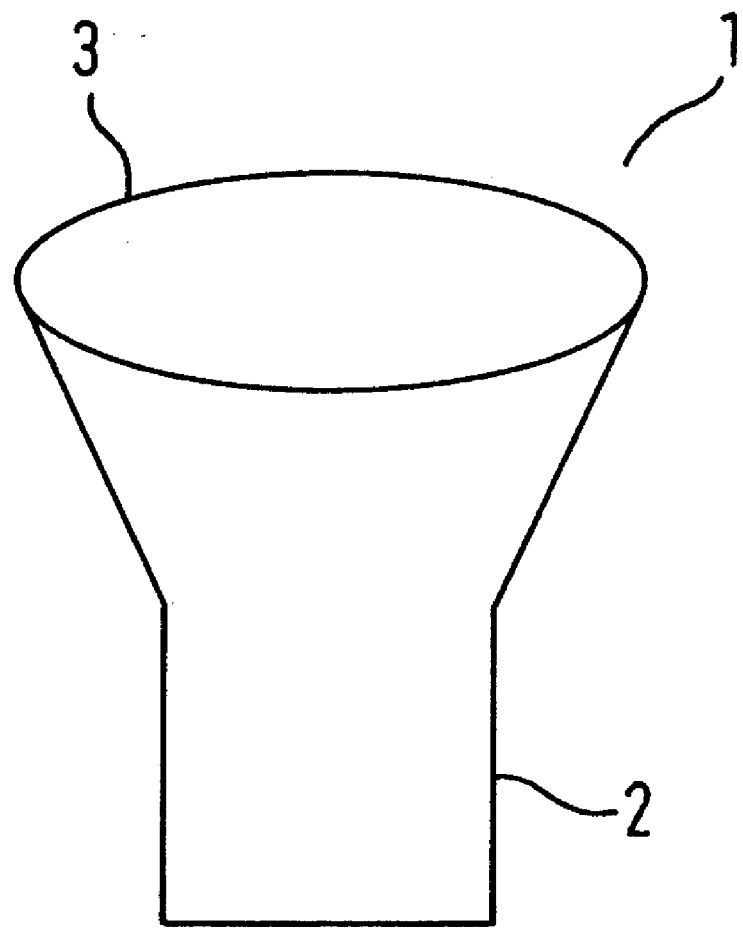
FIG. 1 diagrammatically shows an adapter (1) the lower part (2) of which is placed on one or more projections disposed in a circular to elliptical arrangement surrounding the nozzle or is fixedly connected thereto.
Figure 2:
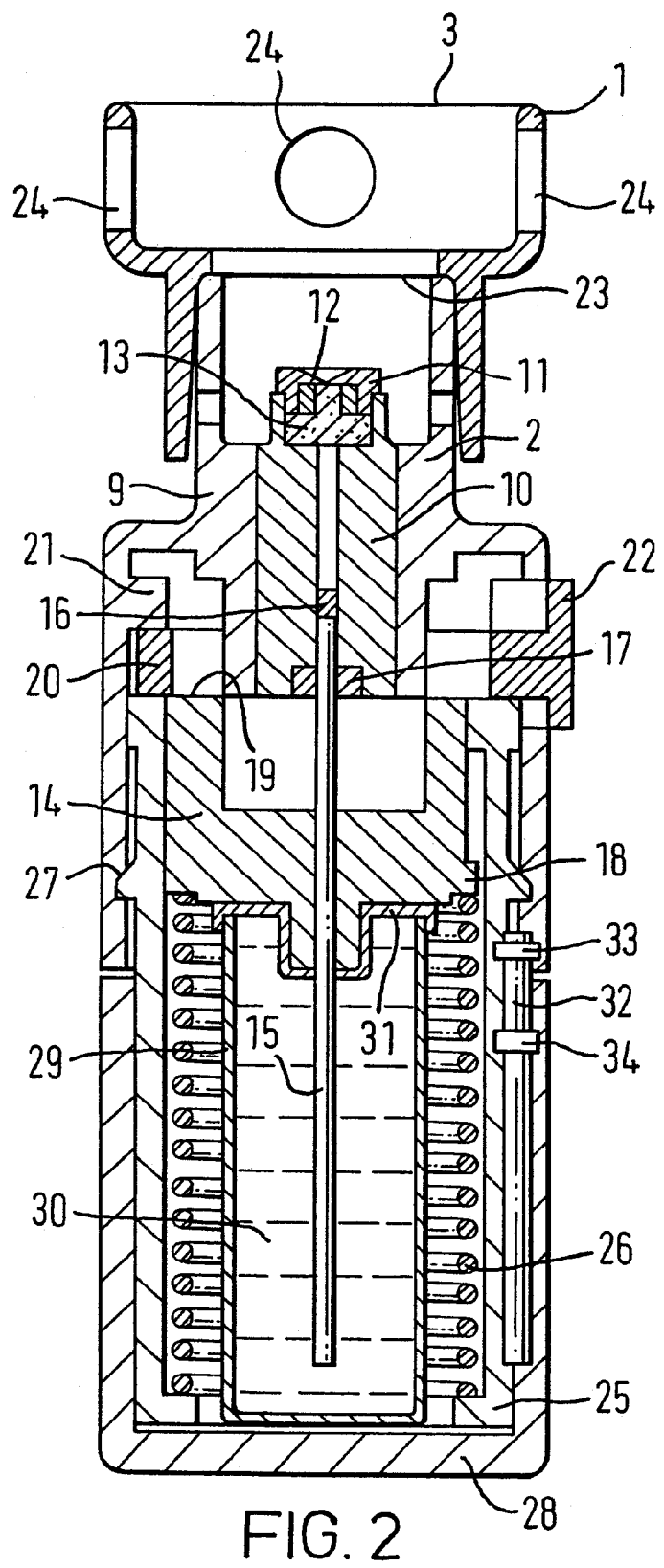
Figure 3:
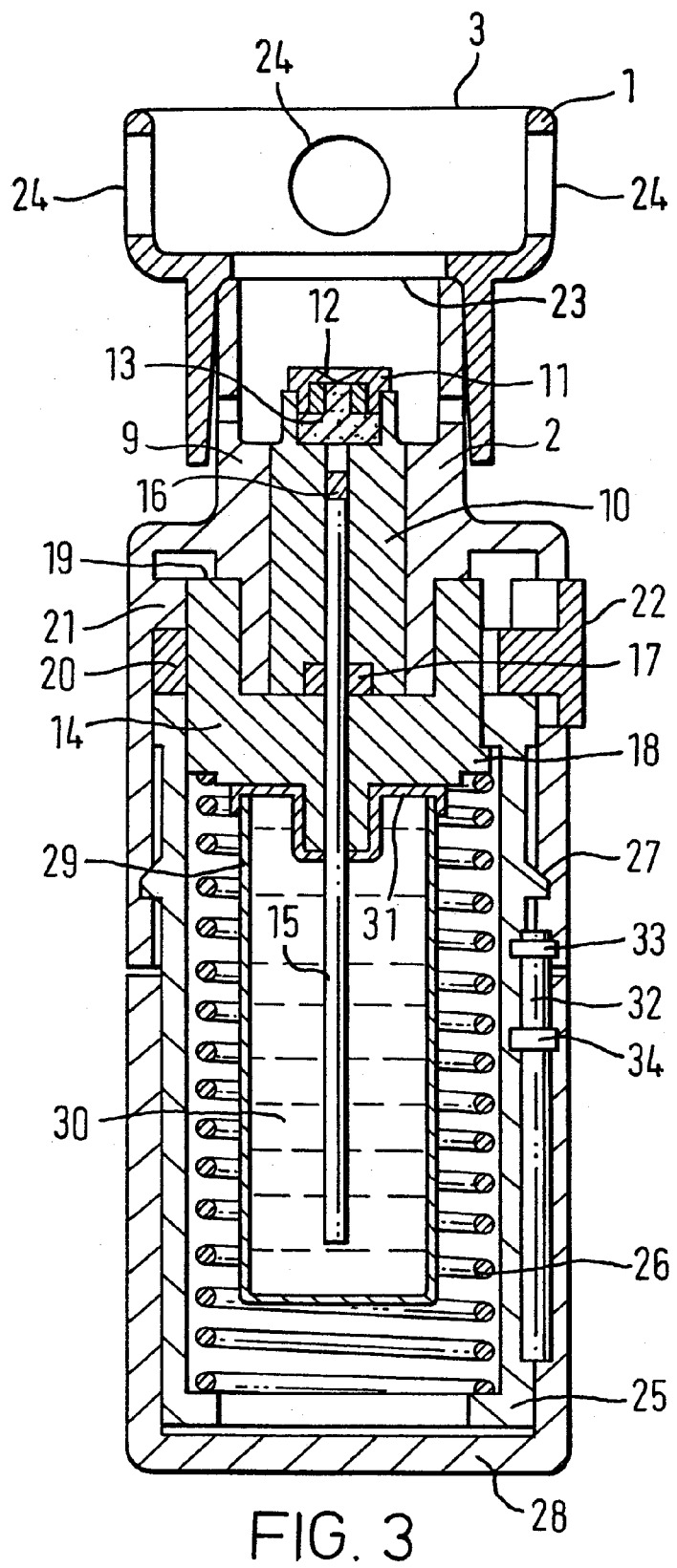

FIGS. 2 and 3 show the atomizer with which the aqueous ophthalmological aerosol preparations may advantageously be administered to the eye.

FIG. 2 shows a longitudinal section through the atomizer with the spring biased, while FIG. 3 shows a longitudinal section through the atomizer with the spring relaxed.

The upper housing part (9) contains the pump housing (10) on the end of which is mounted the holder (11) for the atomizer nozzle. In the holder is the nozzle body (12) and a filter (13). The hollow plunger (15) fixed in the power takeoff flange (14) of the locking mechanism projects partially into the cylinder of the pump housing. At its end the hollow plunger carries the valve body (16). The hollow plunger is sealed off by means of the seal (17). Inside the upper housing part is the stop (18) on which the power takeoff flange abuts when the spring is relaxed. On the power takeoff flange is the stop (19) on which the power takeoff flange abuts when the spring is biased. After the biasing of the spring the locking member (20) moves between the stop (19) and a support (21) in the upper housing part. The actuating button (22) is connected to the locking member. The upper housing part ends in the outlet aperture (23) on which the adapter (1) is placed with its small opening (2). Close to the opening (3) which faces the eye during use, air vents (24) are provided. The open side of the adapter can be closed off by a cover which completely surrounds the openings (3) and (24) from the outside or inside, as selected (not shown).

The spring housing (25) with compression spring (26) is rotatably mounted on the upper housing part by means of the snap-in lugs (27) and rotary bearing. The lower housing part (28) is pushed over the spring housing. Inside the spring housing is the exchangeable storage container (29) for the fluid (30) which is to be atomized. The storage container is sealed off by the stopper (31) through which the hollow plunger projects into the storage container and is immersed at its end in the fluid (supply of active substance solution).

The spindle (32) for the mechanical counter is mounted in the covering of the spring housing. At the end of the spindle facing the upper housing part is the drive pinion (33). The slider (34) sits on the spindle.

The atomizer described above is suitable for atomizing the ophthalmological aerosol preparations to produce an aerosol suitable for administration to the eye.

Any known ophthalmologically active formulations are suitable as the formulation which may be administered using the atomizers according to the invention. These formulations may also differ from the prior art in that the active substances may be more highly concentrated if desired. As mentioned hereinbefore, the quantity of formulation to be administered may be reduced by the process according to the invention from about 50 microlitres in the case of the devices known from the prior art to about 10-20 microlitres or less. This means that the active substance formulations may be about five times more concentrated as a result of the process according to the invention.

In the simplest case the formulation is simply water (water for injections) or isotonic water or other agents for moistening the eye. In other words, there is no pharmacologically active substance present.

Suitable co-solvents may be, inter alia, ethanol, polyethyleneglycols, polypropyleneglycols, ethyleneglycols and propyleneglycols.

The active substances may be, for example, active substances selected from among the antibiotics and anti-infective agents, anticholinergics, antiglaucoma agents, antimycotics, antiseptics, anaesthetics, eye tonics, corticoids and steroids, film-forming agents, vaso-active substances, homoeopathic medicines, mydriatics, NSAID (antiphlogistics), prostaglandins, artificial tears, vitamins and/or virostatics.

Furthermore, any pharmacologically and ophthalmologically acceptable pharmaceutical excipients may be added to the formulations. These include inter alia arufil, benzalkonium chloride, boric acid, calcium chloride, carbomer, chlorhexidine digluconate, citric acid, EDTA, edetic acid salts; glucose, glutathione disulphide, hydroxyethylcellulose, hypromellose, potassium chloride, magnesium chloride, magnesium sulphate, magrocol, mannitol, sodium acetate, sodium chloride, sodium dihydrogen phosphate, sodium hydrogen carbonate, sodium hydroxide, sodium monohydrogen phosphate, sodium tetraborate, sodium thiosulphate, phenylmercury borate, polyethylene oxide, polyoxyethylene-polyoxypropylene copolymer, polysorbate, polyvinyl alcohol, povidone, hydrochloric acid, sorbitol, thiomersal and tyloxapol.

In the case of formulations which contain preservatives, benzalkonium chloride is preferred over EDTA and the salts thereof.

Among the advantages of the process according to the invention are the fact that:
- the risk of irritation or damage to the cornea or the conjunctiva of the eye is reduced when formulations are administered to the eye in this manner;
- ophthalmological formulations are applied uniformly to the surface of the eye, thereby improving absorption by the cornea or the conjunctiva;
- the ophthalmological formulations can be more highly concentrated than conventional eye drops, so that the cornea or conjunctiva of the eye is or are subjected to smaller amounts of unpleasant-feeling foreign matter;
- the dosage can be reproduced very exactly;
- the amount delivered is comparatively small;
- overdosing is avoided;
- systemic side effects are reduced as a result of the small amount applied;
- there is no need for a pumping action towards the eye in order to initiate the spray jet, or the storage bottle has to be pressed manually, i.e. there is no risk that the applicator will accidentally be pressed into the eye;
- no additional force is needed to trigger the spray, as the processes of tensioning the device and administering the formulation are separated from each other in time and functionally;
- each spray actuation is carried out consciously, so that the patient knows how many actuations have been done;
- the aerosol particles have a low pulse and meet the surface of the eye with little force;
- the spray duration is long-lasting and therefore the loss of formulation caused by blinking is slight;
- there is no need to recline the head to administer the formulation;
- there may not be any need for preservatives.

EXAMPLE

The volume of a spray jet delivered with the atomizer described above, known by the trade mark RESPIMAT® is e.g. 12 microlitres and the mass is therefore 0.000012 kg. At a distance of 2 cm from the nozzle the speed of the cloud of droplets as a whole is 3.3 m/s and the pulse is roughly 0.0004 kg*m/s. With a spray duration of 1.2 s a force K of 0.033 milliNewtons is thus obtained, corresponding to a weight of about 3.3 mg.

By comparison, an atomizer which delivers a mass of 0.0001 kg of 0.1 ml and has an average spray duration of 0.12 seconds would generate a cloud of particles with a force of 7.5 milliNewtons, corresponding to a weight of about 750 mg. This presupposes that the nozzle diameter is 0.344 mm and the droplets produced are 100 microns in size. This results in a speed of the cloud of particles of about 9 m/s. The large droplets are hardly slowed down at all before making contact with the eye.

What is claimed is:

1. An atomizer that does not require the use of a propellant for administering a spray mist with small particle size and low speed to the cornea or conjunctiva of the human or animal eye comprising:
   an upper housing part,
   a locking mechanism situated in the upper housing part,
   a spring housing with a spring contained therein, which spring housing is rotatably mounted on the upper housing part,
   a pump housing which is secured in the upper housing part and which comprises at one end a nozzle body with a nozzle or nozzle arrangement,
   a hollow plunger with valve body,
   a power takeoff flange in which the hollow plunger is secured and which is located in the upper housing part,
   a lower housing part which is fitted onto the spring housing in the axial direction,
   a storage vessel for the liquid to be administered, and
   an adapter in the form of a cavity surrounded by a side wall with two openings,
   wherein
      one opening surrounds the nozzle in such a way that a jet spray emerging therefrom is conveyed exclusively into the cavity and
      the second opening, which is opposite from the first, has an outer contour that is such that the second opening surrounds the visible part of the eye of a person or animal without directly touching the eye
   whereby the spray mist is administered to the cornea or conjunctiva of the human or animal eye by the atomizer without the use of a propellant, and whereby the spray mist has an average particle size between about 1 and about 20 microns and an average particle speed, at a spacing from the nozzle of about 1 about 5 cm, of no more than about 50 meters per second.

2. The atomizer according to claim 1, wherein the second opening of the adapter comprises an outer contour that is oval in plan view and in cross section takes the form of a concave curved line with a longer end and a shorter end.

3. The atomizer according to claim 1, wherein the adapter is indivisibly attached to the atomizer as an integral part thereof.

4. The atomizer according to claim 1, wherein the adapter is fitted onto a projection close to the nozzle.

* * * * *